United States Patent [19]

Hewitt et al.

[11] 4,385,914

[45] May 31, 1983

[54] PROCESS AND APPARATUS FOR INCREASING THE CONCENTRATION OF ALCOHOL IN AQUEOUS SOLUTION

[75] Inventors: Frank A. Hewitt, Derby; Keith G. Tillen, Mickleover, both of England

[73] Assignee: Rolls-Royce Limited, London, England

[21] Appl. No.: 323,475

[22] Filed: Nov. 20, 1981

[30] Foreign Application Priority Data

Dec. 3, 1980 [GB] United Kingdom ............... 8038744

[51] Int. Cl.³ .............................................. B01D 9/00
[52] U.S. Cl. ........................................ 62/536; 62/541
[58] Field of Search ................ 62/532, 533, 536, 541; 23/295 R, 296, 300

[56] References Cited

U.S. PATENT DOCUMENTS

| | | | |
|---|---|---|---|
| 2,666,304 | 1/1954 | Ahrel | 62/536 |
| 3,098,735 | 7/1963 | Clark | 62/536 |
| 3,178,899 | 4/1965 | Torobin et al. | 62/536 |
| 3,368,362 | 2/1968 | Smith | 62/536 |

*Primary Examiner*—Frank Sever
*Attorney, Agent, or Firm*—Cushman, Darby & Cushman

[57] ABSTRACT

The process involves the steps of:
 spraying droplets of an aqueous alcohol input solution through spray-bars into a heat transfer fluid contained within a refrigerated process vessel and allowing the droplets to fall through the heat transfer fluid so that some of the water separates out as ice in the droplets;
 collecting the droplets as a slurry of ice and concentrated solution at the bottom of the process vessel and
 subsequently removing the ice to produce a concentrated output solution from the process.

The process can be repeated in subsequent process stages up to a limiting concentration of 92% by weight of alcohol in the case of ethanol. The invention includes apparatus in which the process can be performed. Means by which the efficiency of the process may be optimized are also included.

9 Claims, 4 Drawing Figures

-18.5 etc. = enthalpy (cals/gm of input liquor) relative to input liquor at 30°C
83.7 etc. = heat flow (cals/gm of input liquor) in heat pump systems

PROCESS AND APPARATUS FOR INCREASING THE CONCENTRATION OF ALCOHOL IN AQUEOUS SOLUTION

This invention relates to the concentration of alcohol in aqueous solution by using a low-temperature freeze-separation process and apparatus.

The possible production of very large quantities of ethanol from plant starch and sugar in the future will be dependent on the availability of energy-efficient separation processes in order to separate out the ethanol from the products of fermentation. Currently, large scale distillation processes and freeze-separation processes are energy-inefficient and require bulky plant and equipment. There is a need for efficient readily transportable separation plant in order to avoid the need to transport large quantities of the ethanol/water solution or vegetable feedstock to the plant, since a transportable separation plant can be moved from area to area as the feedstock is harvested and fermented.

The present invention facilitates an energy-efficient low-temperature freeze-separation process which can also be designed to be compact in terms of the separation plant required, and thus readily transportable.

According to the present invention a process for increasing the concentration of alcohol in aqueous solution involves the steps of:

allowing droplets of an input solution to fall through a refrigerated heat transfer fluid, whereby some of the water separates out as ice in the droplets;

collecting the droplets as a mixture of ice and cooled concentrated solution after the droplets have fallen through the heat transfer fluid; and removing the ice to produce a concentrated output solution from the process.

Preferably, the above recited process steps are repeated in each of a plurality of successive process stages, the output solution from each stage except the last stage being fed to the next succeeding stage and the heat transfer fluid in any given stage being maintained colder than the heat transfer fluid in any preceeding stage so that the concentration of the output solution is increased at each stage.

Preferably, there are two or three successive process stages.

The above process is suitable for the concentration of ethanol solutions.

The invention also includes apparatus capable of performing the above process.

The droplets are produced by spraying the input solution into the heat transfer fluid through holes in spray means, the holes preferably being about 1 mm in diameter. Dropletisation of the solution and the resulting intimate contact between the droplets and the refrigerated heat transfer fluid results in rapid and efficient transfer of heat from the droplets to the surrounding heat transfer fluid, which in turn loses heat to refrigeration means.

Although a dense gas could be utilised as the heat transfer fluid, a liquid is preferred, the liquid being immiscible with, and less dense than, the input and output solutions in the process. Examples of suitable heat transfer liquids are kerosine, petrol, hexane and pentane, the particular liquid being selected to cope with the temperature and physical properties of the output solution.

Ice can conveniently be removed from the output solution by passing the solution through filter means, and in order to maximise the efficiency of the process, the ice so removed is preferably utilised as a heat sink for refrigeration of the heat transfer fluid. Likewise, the concentrated output solution can also be utilised as a heat sink for refrigeration of the heat transfer fluid.

Advantageously, the droplets are caused to fall through the heat transfer fluid within vertically disposed duct means immersed in the fluid. The descent of the droplets within the duct means induces circulation of the heat transfer fluid so that it moves downwards within the duct means and upwards outside it, the heat transfer fluid giving up heat to refrigeration means whilst outside the duct means and taking heat from the droplets whilst within the duct means.

An embodiment of the invention will now be described, by way of example only, with reference to the accompanying drawings, in which.

The drawings are not to scale.

In the following description the initial concentration of ethanol in aqueous solution before processing is assumed to be 10% by weight of ethanol, aqueous solutions of ethanol being referred to as "liquor".

It is also assumed that the input liquor to the process has already been filtered to remove impurities such as vegetable matter.

Figure 1:
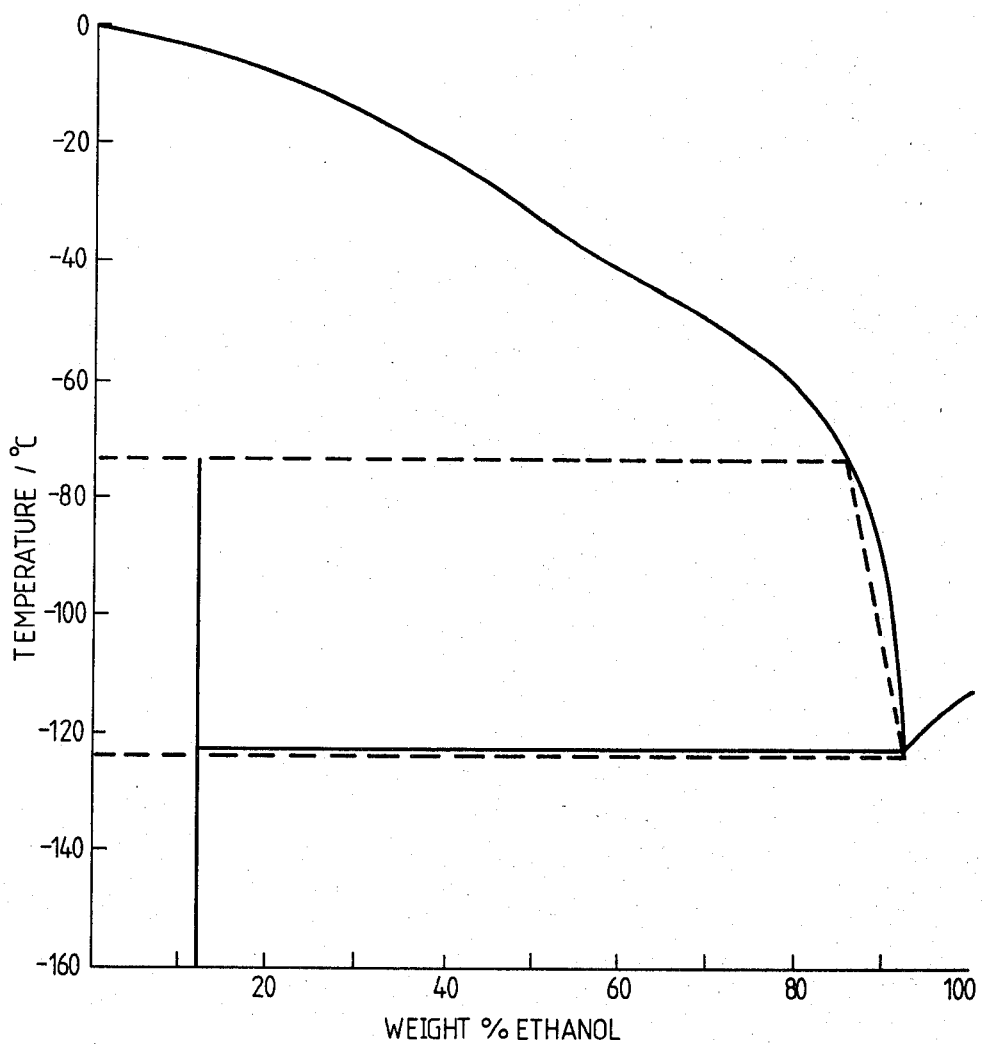
FIG. 1 shows the temperature/composition phase diagram for the ethanol/water system.

Referring to FIG. 1, the equilibrium diagram for the ethanol/water system is taken from a paper by Potts and Davidson, J. Phys. Chem, 69, 996, (1965). On this basis, concentrations from 85% by weight of ethanol at $-70°$ C. to 92% by weight at $-120°$ C. should be obtainable by freeze-separation processes. The present embodiment employs either two or three process stages, depending on the degree of purity required in the final alcohol product. Each process stage increases the concentration of ethanol in the liquor and comprises a process vessel producing an output slurry of ice and ethanol-enriched liquor, followed by filtration equipment which removes the ice, so producing the concentrated output liquor from the stage.

Figure 2:
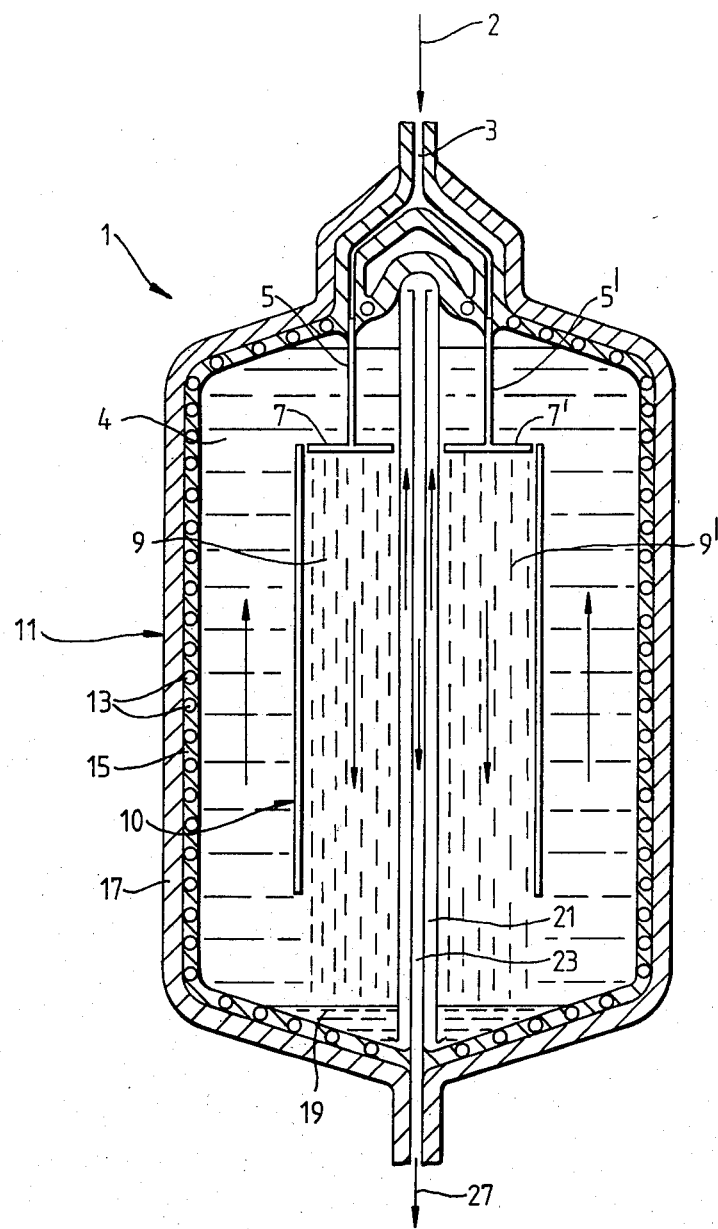
FIG. 2 is a diagramatic longitudinal cross-section of a vessel in which the freeze-separation process occurs.

A typical process vessel 1 is shown in FIG. 2. The vessel 1 contains a separation column 10, which is merely a vertically disposed duct immersed within a heat transfer fluid 4 which fills vessel 1. The input liquor is fed at 2 to inlet manifold 3 and distributed through pipes 5, 5' to spray bars 7,7' which inject streams of droplets 9,9' into the separation column 10. The holes in the spray bars are about one millimeter in diameter.

The heat transfer fluid 4 which fills vessel 1 is a liquid which is immiscible with aqueous solutions of ethanol, examples of heat transfer liquids being quoted later. There is a fairly small difference in density between the injected liquor droplets 9,9' and the heat transfer fluid, which causes the droplets to fall slowly to the bottom of the column 10, losing heat to the heat transfer fluid 4 as they descend. In turn, the heat transfer fluid is refrigerated by extraction of heat from the wall 11 of the vessel 1 by a heat exchange medium which circulates through pipes 13 in a coolant jacket component 15 of wall 11. The other component of wall 11 is an insulating jacket 17, which completely surrounds the vessel 1, including the inlet manifold 3. A heat pump circulates the heat exchange medium through pipes 13 and rejects the heat so gained to a heat sink as described later.

Since the droplets are immiscible with the heat transfer fluid, they remain as discrete droplets during their descent of the column 10. The heat transfer fluid acts to prevent the drops from coalescing with each other as they descend, and slows their descent velocity. The small size, discrete nature and slow descent of the droplets ensures efficient transfer of heat to the heat transfer fluid and thus allows the separation column and its container vessel to be compact in size.

By the time the droplets 9, 9' reach the bottom of column 10 some of the water has separated out as ice and the droplets collect in a pool 19 at the bottom of vessel 1 in the form of a slurry of ice crystals and enriched liquor.

As the droplet streams 9,9' are injected they displace the heat transfer fluid and also tend to drag it with them as they descend the column 10, thus inducing the necessary internal circulation of the slurry and the heat transfer fluid within the column as shown by the arrows. Therefore, as the injection of the droplet streams 9,9' continues, the slurry is forced up an annular pipe 21, which is the outer one of two concentric pipes 21 and 23. As the slurry travels up annular pipe 21 it helps in cooling the upper regions of the column, and thereafter runs out of the vessel 1 down the central pipe 23. The function of the vertical duct which comprises separating column 10 is to control circulation of the heat transfer fluid within vessel 1, the descent of the droplets 9,9' causing a downflow of heat transfer fluid in the column due to viscous drag between droplets and fluid, and a corresponding upflow of fluid around the outside of the column.

After passing out of the vessel 1 at 27, the slurry falls into a centrifugal filter (not shown), having a small-pored sintered filter drum for efficient separation of the ice crystals from the ethanol-enriched liquor. In order to effect continuous removal of the ice from the drum surface, a helical scraper fits within it and scrapes the ice off as the drum revolves. After this, the filtered enriched liquor either passes to the next stage of the process or, if the final stage has been reached, is passed through heat exchangers as a heat sink for the hot side of the heat-pump systems which circulate the heat exchange medium through pipes 13 in walls 11 of the two or three separating column vessels 1. The enriched liquor is finally removed from the system at near ambient temperature. Similarly, the removed ice is also used in the cooling processes, being removed from the system as water.

The liquor quantities and temperatures at each stage in a three-stage process are listed in the Table below.

TABLE

| Stage | Temp/°C. | Input liquor mass | Output liquor mass | Output liquor concn. % by wt. ethanol |
|---|---|---|---|---|
| 1 | −25 | N | 0.286 N | 35 |
| 2 | −75 | 0.286 N | 0.118 N | 85 |
| 3 | −115 | 0.118 N | 0.109 N | 92 |

Figure 3:
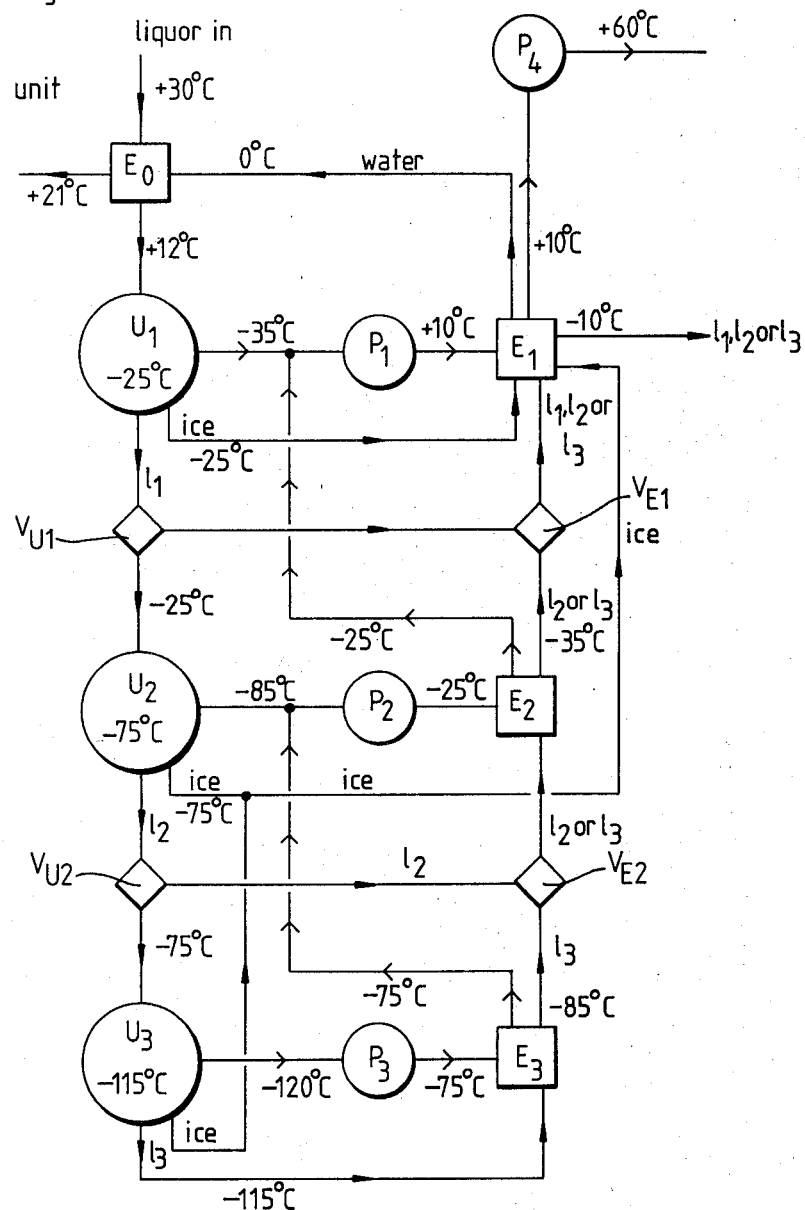
FIG. 3 is a flow chart of a complete multi-stage system indicating process temperatures.

The material flows and heat flows involved in a complete system with three process stages will now be described in more detail with reference to the flow diagrams in FIGS. 3 and 4. On the flow lines in both Figures, solid arrows represent material transfer and open arrows represent energy transfer.

In the illustrated three-stage system, there are three process units $U_1$, $U_2$ and $U_3$ in series with each other, each one comprising a process vessel and its associated centrifugal filter. Each process vessel is refrigerated by its associated heat pump $P_1$, $P_2$, $P_3$ respectively, and these heat pumps reject heat through associated heat exchangers $E_1$, $E_2$ and $E_3$, which use ice and/or cold liquor as heat sinks.

When all three stages of the system are working, cold concentrated liquor $l_3$ from the final process unit $U_3$ is used as a heat sink for the heat pumps at all three stages, being passed through exchangers $E_3$, $E_2$ and $E_1$ in series before it issues from the system in its final condition via exchanger $E_1$. The quantity of ice separated out at process unit $U_3$ is too small to be practically employable in a heat exchanger by itself, so this ice is fed to the ice output of process unit $U_2$. Depending on detail design considerations, the ice may or may not be used as a heat sink in exchanger $E_2$ of the second stage heat pump $P_2$, but if not is passed for use as a heat sink in exchanger $E_1$ as shown, together with the ice from process unit $U_1$. The cold water resulting from the use of the ice in exchanger $E_1$ is used to pre-cool the incoming warm dilute liquor by means of a further heat exchanger $E_0$ located in the liquor flowline before the first process unit $U_1$.

Insofar as the cold liquor flows $l_1$, $l_2$ and $l_3$ are concerned, heat exchangers $E_1$, $E_2$ and $E_3$ represent heat exchangers of the sort in which the liquor as a heat sink is caused to flow through heat-exchange coils or matrices in order to take away heat from similar coils or matrices on the hot side of heat pumps $P_1$, $P_2$ and $P_3$. However, insofar as the ice is concerned, heat exchanger $E_1$ (and $E_2$ if appropriate) represents a reservoir containing the ice through which heat-exchange coils from heat pump $P_1$ (or $P_2$) are run, the cold water from the melted ice being run off and circulated through heat exchanger $E_0$. Note that the ice is reduced to a powdered state by the helical scrapers in the centrifugal filters, the removed ice being conveyed to the heat-exchange ice reservoir by conveyor belts or other means, such as screw feeds.

The use of ice and liquor from the second and third stages of the system in exchanger $E_1$ conveys heat from these stages up to the first stage, a further heat pump $P_4$ being used to extract heat from exchanger $E_1$ and reject it into the environment. In order to improve efficiency by actively pumping heat up the system to the first stage heat exchanger $E_1$, the cold sides of the heat pumps $P_1$ and $P_2$ are used as heat sinks for the exchangers $E_2$ and $E_3$ respectively.

The system is started up by using heat pump $P_4$ to cool heat exchanger $E_1$, which in turn enables heat pump $P_1$ to cool process unit $U_1$. Once the heat-transfer fluid in heat pump $P_1$ is at operating temperature, heat pump $P_2$ can be started to reduce the temperature in process unit $U_2$. Finally, the sequence is continued to process stage $S_3$, so that the system is cooled to operating temperatures.

To enable start-up of the system one stage at a time in this way, three-way valves $V_{u1}$, $V_{U2}$ and $V_{E1}$, $V_{E2}$ are provided between the stages on the process unit and heat exchanger sides respectively. The valves control the flows $l_1$, $l_2$ and $l_3$ of the liquor from the process units $U_1$, $U_2$ and $U_3$ respectively. After start up of the first stage, and whilst it is working down to operating temperature, the valve $V_{U1}$ passes the liquor $l_1$ coming from process unit $U_1$ over to the valve $V_{E1}$ on the exchanger side, but does not pass it on to the next process unit $U_2$. Valve $V_{E1}$ allows liquor $l_1$ to flow through exchanger $E_1$ to cool the stage, and from thence liquor $l_1$ flows out of the system. When the first stage reaches operating temperature, valve $V_{U1}$ shuts off the liquor flow to the exchanger side and passes it to process unit $U_2$ instead. Similarly, valve $V_{U2}$ passes liquor $l_2$ only to valve $V_{E2}$ until the second stage of the system has reached operating temperature, but thereafter valve $V_{E2}$ passes liquor $l_2$ only to process unit $U_3$.

Figure 4:
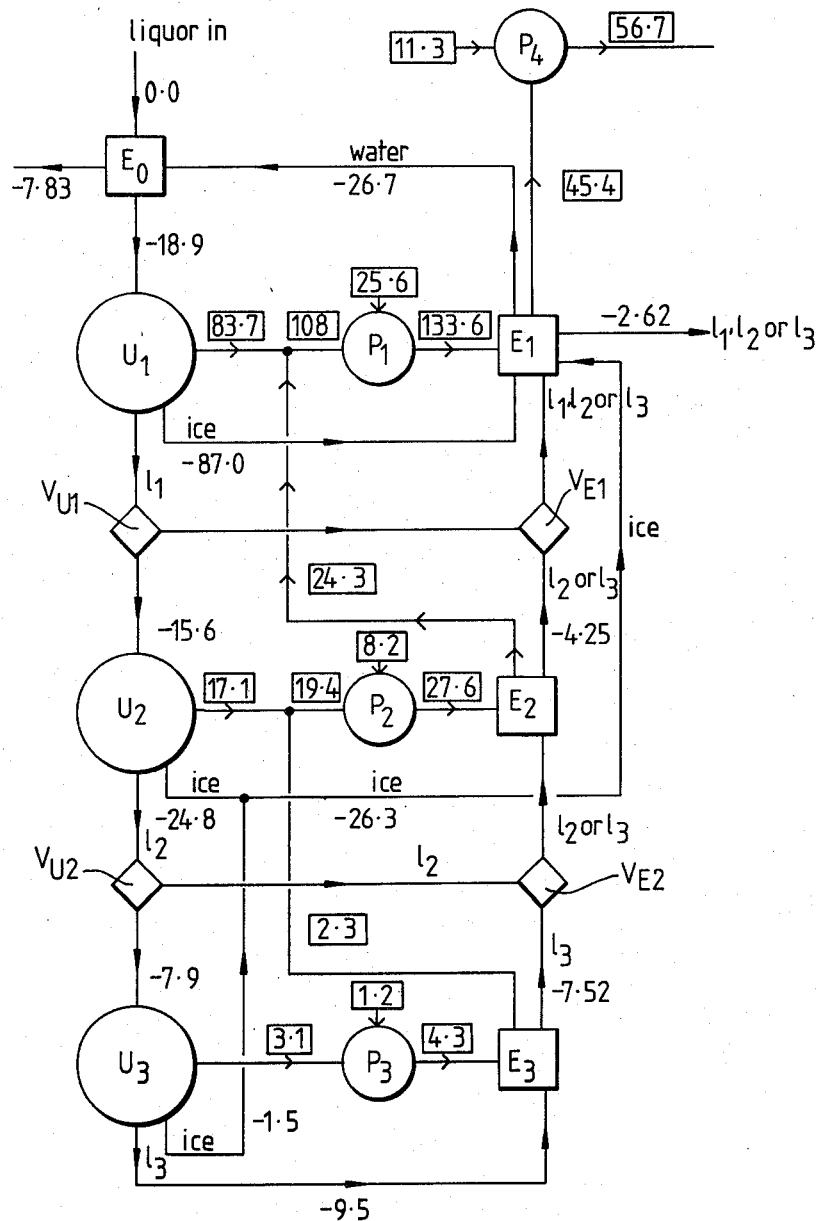
FIG. 4 is the same flow chart, but showing heat flows instead of temperatures.

In FIG. 4, the heat flows in the heat pump systems, including their input powers, are shown as the boxed figures, whilst the enthalpies of the liquor and ice flows relative to the enthalpy of the input liquor are shown as unboxed figures. Both sets of figures are in terms of calories per gramme of input liquor.

Four low density liquids have been judged suitable for use as heat transfer fluids in the process vessels, namely kerosene or petrol for the first stage, petrol, hexane or pentane for the second stage and pentane or petrol for the third stage. Hexane and pentane could also be used in the first stage, but they are of lower density and are more expensive than kerosine or petrol and therefore are more suitable for use in the two later stages, where the density of the output solution and the volume of the process vessels are also lower. Pentane is preferred for use in the third stage because in addition to having a low density it also has a freezing point which is appreciably lower than the temperature of the output solution.

Due to the intimate contact between the heat transfer fluid and the droplets of ethanol solution whilst the droplets are descending the separation column, it is inevitable that a small amount of the heat transfer fluid will pass out of the process vessels together with the ice and the concentrated solution. However, since the four heat-exchange liquids mentioned are immiscible with water they can easily be separated out from the ice melt water or the concentrated output solution in settling tanks if this is thought worthwhile. On the other hand, if the ethanol is to be used as a fuel, impurities of burnable hydrocarbons in the output liquor will not matter. Of course, provision must be made to keep the process vessels topped up with the appropriate heat exchange fluid.

The overall energy costs of the process will now be considered.

The total energy input required for three stages to produce the limiting concentration, 92% by weight of ethanol, is the sum of the heat pump energy inputs, with allowance being made for inefficiencies. The figure involved is thus ~2 MJ/kg ethanol out.

For an idea of the scale involved, at an output of 2000 kg per hour (roughly equivalent to one 5000 gallon tanker load per 10 hour day), the energy input requirement is 1130 kW. If no more than mechanical inefficiencies are considered as adding to this figure, then the following may be considered reasonable:
(i) heat pump compressor efficiencies: 90%
(ii) fluid pumping efficiencies: 85%
(ii) mechanical filtration efficiencies: 80%

The total energies involved at (ii) and (iii) are very small, and will not be considered further, except approximately. The energy input requirement then becomes ~1300 kW, which is a fairly substantial figure. If this energy were to be provided by burning some of the ethanol produced in an internal combustion engine, then heat recovery using an exhaust turbine would be reasonable. The power outputs could be expected to be of the order of 4:1 shaft output to recovered shaft output, with an overall efficiency using modern, efficient designs, of up to 50% of the input fuel energy. This therefore elevates the fuel energy requirement to 2500 kW. This compares with a combustion energy output for the output fuel of 15850 kJ. If the power input requirement were to be met from the fuel produced, around 16% of the product would then be consumed. This compares very favourably with other methods.

The size of the plant and equipment necessary for the process will now be considered.

2000 kg of 92% ethanol per hour is suggested as a useful output of an ethanol refining system. Thus corresponds to a liquor input of around 20 meters$^3$/hour, which in turn would represent the output from about 0.5 hectare of land growing sugar cane at high yield. This input is then around 5.6 liters/sec.

A suitable fluid volume for the process vessels is $10^3 \times$ the input/second. Thus the fluid volume of the process vessel for stage 1 would be 5600 liters, the other stages being smaller as the liquor is concentrated. Appropriate matching sizes for compressors, filters and pumping equipment are chosen. It is assumed that the power will be provided by a carburetted, spark ignition, internal combustion engine, burning ethanol. In this case an engine of around 60 liters cubic capacity should produce the required 1300 kW on a continuous basis. Exhaust gas energy could be extracted using a gas turbine, leading to a total efficiency of around 50% of the energy input. The size and weight of such an engine, taken with that of the rest of the system, should result in a complete assembly, including a filter for the input liquor and associated pumps, which weighs less than 50 tonnes, and would be capable of being transported on a large truck with close-coupled trailer.

Although the above description mentions only the separation of ethanol, i.e. ethyl alcohol, from aqueous mixtures, the invention may also be applicable to the separation of amyl or methyl alcohol from aqueous mixtures, it being necessary to make due allowance for the differences in physical properties between the various alcohols in the various stages of the process, as will be apparent to those skilled in the art.

We claim:
1. A process for increasing the concentration of alcohol in aqueous solution, comprising the steps of:
   (1) providing vertically disposed duct means immersed in said heat transfer fluid which define a volume of said heat transfer fluid interior to said duct means and a volume of said heat transfer fluid exterior to said duct means for allowing droplets of an input solution to fall through a refrigerated heat transfer fluid, such that some water in said droplets separates out as ice in said droplets wherein said droplets fall through said heat transfer fluid within said duct means; said duct means providing means to induce circulation of said heat transfer fluid such that said circulation is between said interior and exterior volumes while further providing means for refrigerating, said heat transfer fluid while moving through said exterior volume and taking heat from said droplets while moving through said interior volume;

(2) collecting said droplets as a mixture of ice and concentrated solution after said droplets have fallen through said heat transfer fluid; and (3) removing said ice to produce a concentrated output solution from the process.

2. A process according to claim 1 in which said heat transfer fluid is a liquid, said liquid being immiscible with, and less dense than, said input solution and said output solution.

3. A process according to claim 2 in which said heat transfer fluid is selected from the group of liquids consisting of kerosine, petrol, hexane and pentane according to the temperature and physical properties of said output solution.

4. A process according to claim 1 in which said process steps are repeated in each of a plurality of successive process stages, said output solution from each stage except the last stage being fed to the next succeeding stage and said heat transfer fluid in any given stage being maintained colder than said heat transfer fluid in any preceeding stage so that the concentrations of said output solution is increased at each said stage.

5. A process according to claim 4 in which there are three process stages.

6. A process according to claim 1 in which said ice is removed from said output solution by passing said output solution through filter means.

7. A process according to claim 1 in which in order to maximise efficiency, said ice removed from said output solution is utilised as a heat sink for refrigeration of said hear transfer fluid.

8. A process according to claim 1 in which in order to maximise efficiency, said concentrated output solution is utilised as a heat sink for refrigeration of said heat transfer fluid.

9. A process according to claim 1 in which said heat transfer fluid in step (1) moves downwards within said duct means and upwards externally thereof, said heat transfer fluid giving up heat to said refrigeration means while moving upwards outside said duct means, and taking heat from said droplets while moving downwards within said duct means.

* * * * *